(12) United States Patent
McGrail et al.

(10) Patent No.: US 7,201,168 B2
(45) Date of Patent: Apr. 10, 2007

(54) NON-TRACHEAL VENTILATION TUBE

(75) Inventors: Thomas W. McGrail, Cicero, IN (US); Voelker Bertram, Sulz (DE)

(73) Assignee: King Systems Corporation, Noblesville, IN (US)

( * ) Notice: Subject to any disclaimer, the term of this patent is extended or adjusted under 35 U.S.C. 154(b) by 0 days.

(21) Appl. No.: 11/104,361

(22) Filed: Apr. 12, 2005

(65) Prior Publication Data

US 2005/0229933 A1   Oct. 20, 2005

Related U.S. Application Data

(60) Provisional application No. 60/562,169, filed on Apr. 14, 2004.

(51) Int. Cl.
*A61M 16/00* (2006.01)

(52) U.S. Cl. ............................. 128/207.14; 128/200.26

(58) Field of Classification Search .......... 128/207.15, 128/207.14, 200.26, 207.16; 604/96.01, 604/101.01, 102.02
See application file for complete search history.

(56) References Cited

U.S. PATENT DOCUMENTS

| | | | | |
|---|---|---|---|---|
| 1,567,500 A | 12/1925 | Hein | ..................... | 128/207.15 |
| 2,099,127 A | 11/1937 | Leech | ..................... | 128/207.15 |
| 3,363,629 A | 1/1968 | Kuhn | ..................... | 128/207.15 |
| 3,616,799 A | 11/1971 | Sparks | ..................... | 128/207.15 |
| 3,659,612 A | 5/1972 | Shiley et al. | ..................... | 128/207.15 |
| 3,799,173 A | 3/1974 | Kamen | ..................... | 128/207.15 |
| 3,810,474 A | 5/1974 | Cross | ..................... | 128/207.15 |
| 3,989,571 A | 11/1976 | Harautuneian | ..................... | 156/250 |
| 4,090,518 A * | 5/1978 | Elam | ..................... | 128/207.15 |
| 4,230,108 A | 10/1980 | Young | ..................... | 128/207.15 |
| 4,231,365 A * | 11/1980 | Scarberry | ..................... | 128/207.15 |
| 4,327,720 A * | 5/1982 | Bronson et al. | ..................... | 128/207.15 |
| 4,584,998 A | 4/1986 | McGrail | ..................... | 128/207.15 |
| 4,627,433 A | 12/1986 | Lieberman | | |
| 4,688,568 A | 8/1987 | Frass et al. | ..................... | 128/207.15 |
| 4,976,261 A | 12/1990 | Gluck et al. | | |
| 4,979,505 A | 12/1990 | Cox | | |
| 5,067,497 A * | 11/1991 | Greear et al. | ..................... | 128/207.15 |
| 5,301,667 A | 4/1994 | McGrail et al. | ..................... | 128/205.14 |

(Continued)

FOREIGN PATENT DOCUMENTS

DE        29521244 U1    10/1996

(Continued)

*Primary Examiner*—Teena Mitchell
(74) *Attorney, Agent, or Firm*—E. Victor Indiano; Indiano Vaughan LLP

(57) ABSTRACT

A non-tracheal ventilation tube includes a multi-lumen tube shaft having a proximal end and a distal end, a proximal cuff and a distal cuff. The multi-lumen tube shaft is separated into a ventilation channel extending from a proximal ventilation opening to a distal ventilation opening, a suction channel extending from a proximal suction opening to a distal suction opening, and an inflation channel. The proximal cuff is attached to the tube shaft and is connected to the inflation channel for inflation and deflation. The distal cuff is attached to the tube shaft on the distal side of the proximal cuff and is connected to the inflation channel for inflation and deflation. The proximal suction opening and the proximal ventilation opening are located on the proximal side of the proximal cuff. The distal suction opening is located on the distal side of the distal cuff. The distal ventilation opening is located between the proximal cuff and the distal cuff. The outside diameter of the tube shaft decreases between the proximal cuff and the distal cuff due to the ending of the ventilation channel.

30 Claims, 8 Drawing Sheets

U.S. PATENT DOCUMENTS

| | | | |
|---|---|---|---|
| 5,309,906 A * | 5/1994 | LaBombard | 128/207.14 |
| 5,392,774 A | 2/1995 | Sato | 128/207.15 |
| 5,499,625 A * | 3/1996 | Frass et al. | 128/207.15 |
| 5,632,271 A | 5/1997 | Brain | |
| 5,642,730 A | 7/1997 | Baran | |
| 5,743,258 A | 4/1998 | Sato et al. | 128/207.15 |
| 5,819,733 A | 10/1998 | Bertram | 128/207.15 |
| 5,865,176 A * | 2/1999 | O'Neil | 128/207.15 |
| 5,937,859 A | 8/1999 | Augustine et al. | 128/207.15 |
| 6,062,223 A * | 5/2000 | Palazzo et al. | 128/207.15 |
| 6,070,581 A | 6/2000 | Augustine et al. | 128/207.15 |
| 6,119,695 A | 9/2000 | Augustine et al. | 128/207.15 |
| 6,311,688 B1 | 11/2001 | Augustine et al. | 128/200.26 |
| 6,338,343 B1 | 1/2002 | Augustine et al. | 128/207.15 |
| 6,427,686 B2 | 8/2002 | Augustine et al. | 128/200.26 |
| 6,830,049 B2 | 12/2004 | Augustine et al. | 128/207.15 |
| 2001/0013345 A1* | 8/2001 | Bertram | 128/200.26 |
| 2001/0054425 A1* | 12/2001 | Bertram | 128/207.15 |
| 2002/0011249 A1 | 1/2002 | Augustine et al. | 128/207.15 |
| 2002/0189618 A1 | 12/2002 | Augustine et al. | 128/207.15 |
| 2005/0150505 A1 | 7/2005 | Burrow et al. | 128/911 |
| 2005/0229933 A1 | 10/2005 | McGrail et al. | 128/207.14 |

FOREIGN PATENT DOCUMENTS

| | | |
|---|---|---|
| DE | 19537735 C1 | 1/1997 |
| DE | 19962985 C1 | 12/2000 |
| DE | 19962372 A1 | 7/2001 |
| DE | 10039045 C1 | 9/2001 |
| DE | 10019956 A1 | 10/2001 |
| DE | 19962372 C2 | 6/2002 |
| DE | 10019956 C2 | 7/2002 |
| FR | 2755615 A1 | 5/1998 |
| FR | 2807947 A1 | 10/2001 |
| GB | 2319182 B | 10/2000 |
| GB | 2364915 B | 2/2004 |
| JP | 10179745 | 7/1998 |
| JP | 11235383 | 8/1999 |
| JP | 11267222 | 10/1999 |

* cited by examiner

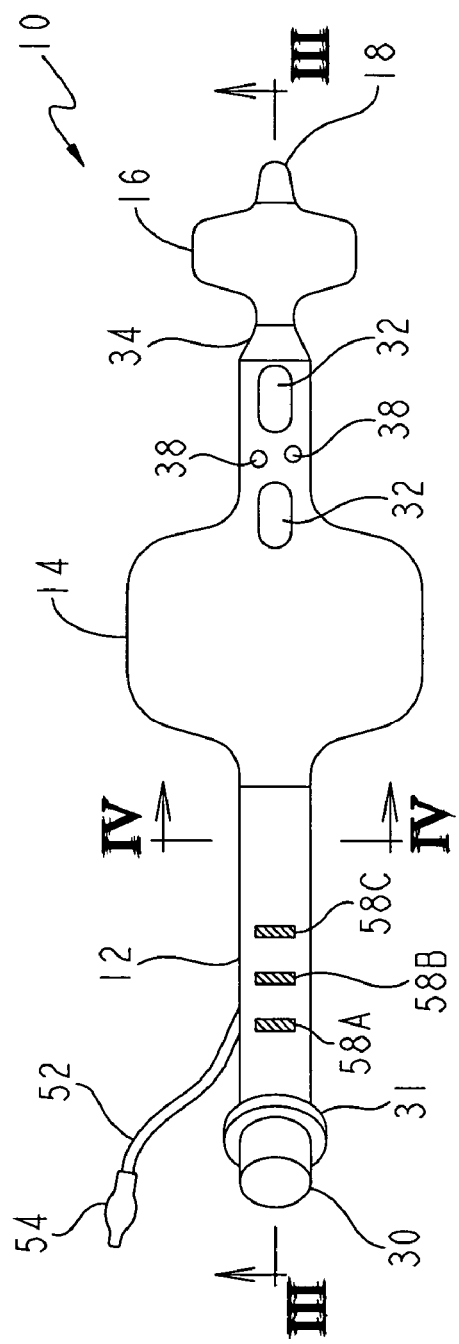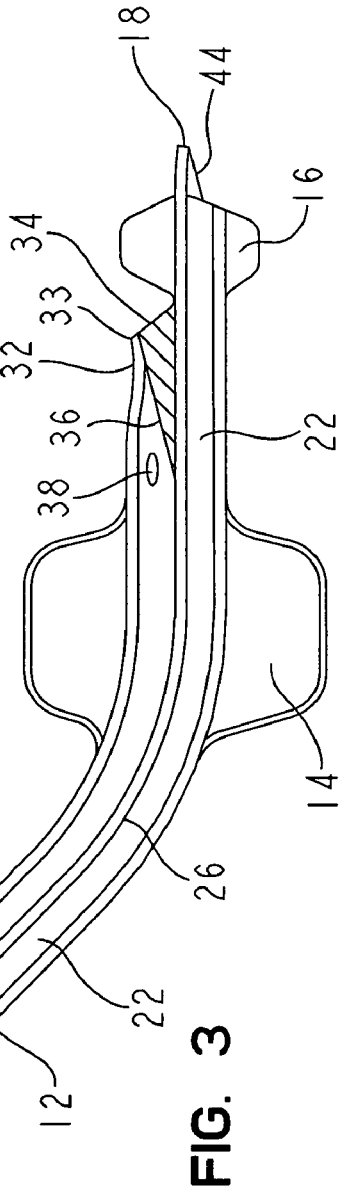
FIG. 2
FIG. 3

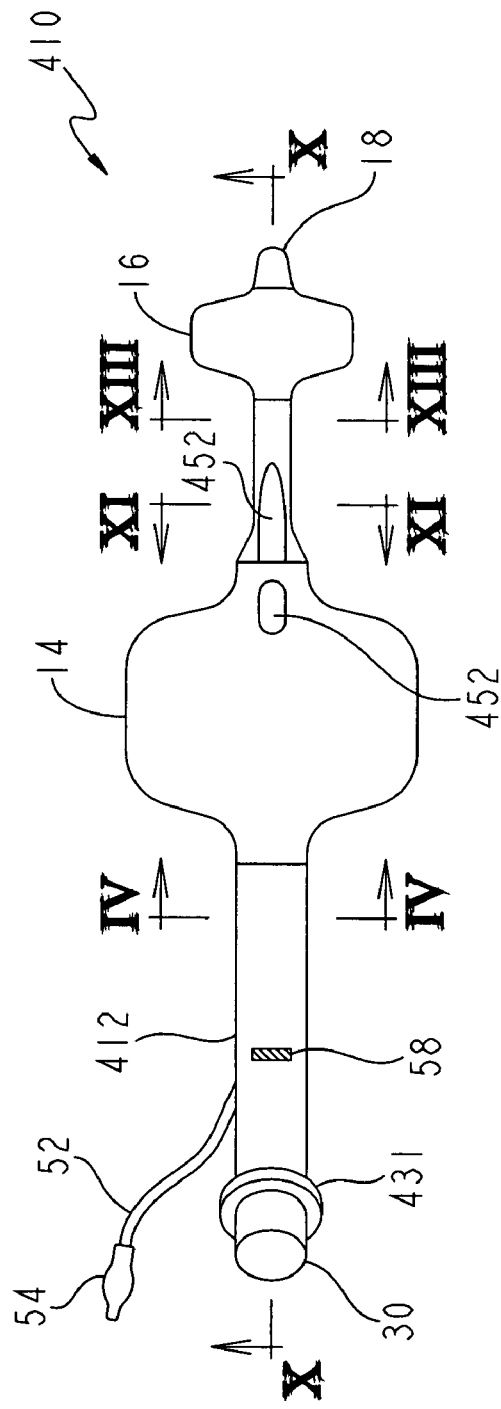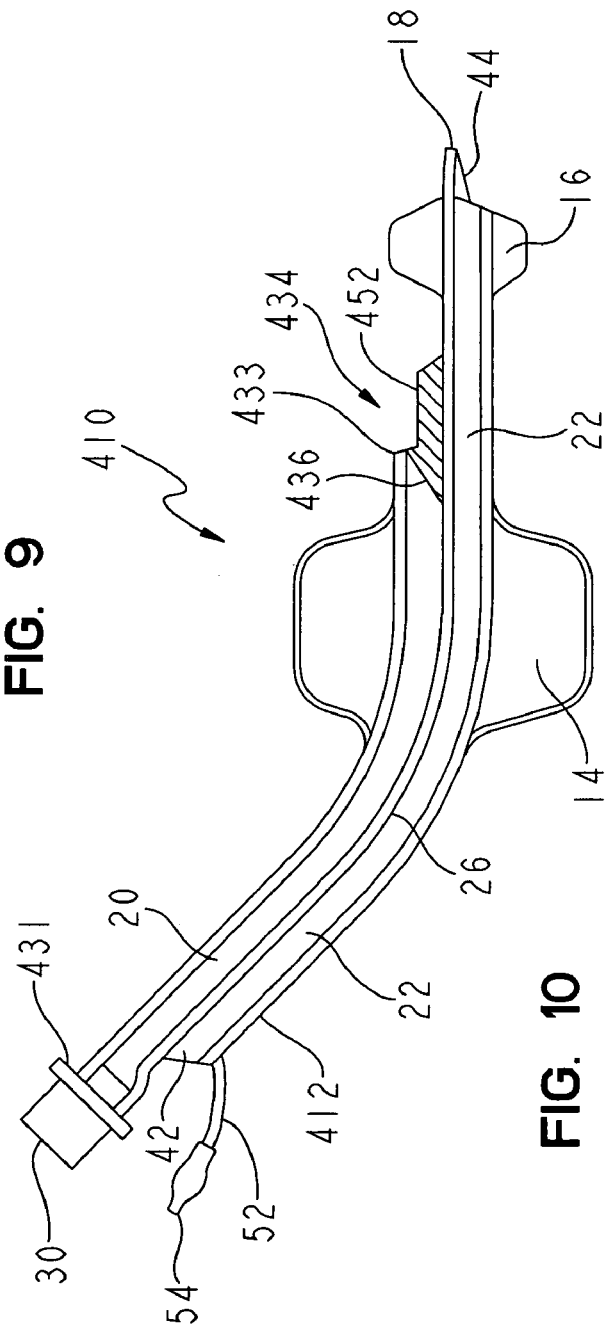
FIG. 9
FIG. 10

NON-TRACHEAL VENTILATION TUBE

I. CLAIM OF PRIORITY

This application claims priority to Thomas W. McGrail U.S. Provisional Application No. 60/562,169 which was filed on 14 Apr. 2004

TECHNICAL FIELD OF THE INVENTION

The present invention relates to a non-tracheal ventilation tube, and in particular, to a non-tracheal ventilation tube for anesthesia or resuscitation comprising an inflatable proximal cuff for blocking the pharynx, an inflatable distal cuff for blocking the entrance to the esophagus, and a multi-lumen tube shaft providing separate channels with access to the trachea and the esophagus.

III. BACKGROUND OF THE INVENTION

A multi-lumen non-tracheal ventilation tube having two inflatable cuffs and an application opening disposed between the cuffs has become well known in the art. These devices are used in emergency resuscitations, application of anesthesia in operating theaters, and other situations requiring artificial respiration of a patient, or controlled access to the trachea and/or esophagus.

The cuffs are inflated to provide a gas and liquid-tight sealing of the entrance to the trachea from the pharynx and the esophagus. One lumen of the tube forms an ventilation channel providing access to the entrance of the trachea. This ventilation channel facilitates artificial respiration of the patient, and can be used to introduce respiratory anesthetics to the patient with the inflated cuffs blocking the anesthetics from escaping into the surrounding environment through the pharynx or into the stomach through the esophagus. Another lumen of the tube forms a suction channel providing access to the entrance of the esophagus. The separate channels and the inflated distal cuff prevent the escape of stomach contents into the trachea.

U.S. Pat. No. 5,819,733 discloses a single lumen transpharyngeal tube for introducing substances into the trachea of the patient while blocking the pharynx and the esophagus of the patient. The transpharyngeal tube includes a tube shaft, and an inflatable primary cuff for blocking the pharynx and an inflatable secondary cuff for blocking the esophagus both disposed on the tube shaft. The tube shaft has an S-shaped longitudinal profile and an application opening located between the two cuffs. The inflatable secondary cuff completely surrounds the tube tip. When the transpharyngeal tube is properly introduced into the patient the inflated secondary cuff blocks the esophagus and the inflated primary cuff blocks the pharynx, and access to the trachea is provided through the application opening of the tube shaft.

U.S. Pat. No. 5,499,625 discloses a dual lumen airway having an inflatable distal cuff and an inflatable pharyngeal cuff for providing access to the entrance of both the trachea and the esophagus. The distal end of the dual lumen airway can be inserted into either the trachea or the esophagus. The proximal ends of each lumen are separate and provide independent access to each lumen. The dual lumens run parallel along the length of the airway. One lumen is open at the distal end, while the other lumen is closed at the distal end but has an air outlet which, when the airway is properly inserted, is located in a patient's pharyngeal area. The inflatable distal cuff is located adjacent the distal end of the tube, and the inflatable pharyngeal cuff is located between the air outlet of the closed tube and the proximal end of the airway. When the airway is properly introduced into a patient with the distal end of the airway extending into the entrance of the esophagus, the inflated pharyngeal cuff blocks the pharynx from the trachea, the inflated distal cuff blocks the esophagus from the trachea, and the lumen with the open end provides access to the esophagus, the lumen with the closed end provides access to the trachea through the air outlet.

U.S. Pub. No. 2001/0054425 discloses a hyperpharyngeal tube for intubation anesthesia including two inflatable cuffs, and a tube shaft that is divided into a suction channel and a respiratory channel. The first cuff is inflated to seal the naso- and oro-pharynx and to fix the hyperpharyngeal tube in the pharynx; and the second cuff is inflated to seal the esophagus. The suction channel provides access to the esophagus for removing secretions or foreign bodies from the esophagus, and the respiratory channel provides access to the trachea for guiding respiratory air into the trachea.

These aforementioned devices provide controlled access to the trachea, and in some cases to the esophagus. However, the extent and circumference of the aforementioned tubes can cause irritation to the patient, especially at the entrance of the esophagus. The lumens of the tubes are not sized and shaped for maximizing utility of the inside diameter of the ventilation and suction channels. The patient's epiglottis or other laryngeal tissue can cause blockage of the ventilation or respiratory channel opening to the trachea causing insufficient respiratory gases to reach the patient. Airway patency can be especially challenging for a patient breathing spontaneously.

To overcome these and other issues with the current state of non-tracheal ventilation tubes, the Applicants sought to provide an improved non-tracheal ventilation tube which is described in the present application.

IV. SUMMARY OF THE INVENTION

In accordance with the present invention a non-tracheal ventilation tube is disclosed. The non-tracheal ventilation tube includes a multi-lumen tube shaft, a proximal cuff and a distal cuff. The multi-lumen tube shaft has a proximal end and a distal end, and is separated into a ventilation channel, a suction channel and an inflation channel. The proximal cuff is attached to the tube shaft and is connected to the inflation channel for inflation and deflation of the proximal cuff. The distal cuff is attached to the tube shaft on the distal side of the proximal cuff and is connected to the inflation channel for inflation and deflation of the distal cuff. The ventilation channel extends from a proximal ventilation opening on the proximal side of the proximal cuff to a distal ventilation opening between the proximal cuff and the distal cuff. The suction channel extends from a proximal suction opening on the proximal side of the proximal cuff to a distal suction opening on the distal side of the distal cuff. The outside diameter of the tube shaft decreases between the proximal cuff and the distal cuff due to the ending of the ventilation channel.

When the non-tracheal ventilation tube is inserted in the airway of a patient the proximal and distal cuffs are inflated to the desired pressures through the inflation channel. When the non-tracheal ventilation tube is properly positioned, the proximal cuff blocks the oropharynx and the nasopharynx from the openings of the esophagus and the trachea, and the distal cuff blocks the opening of the esophagus from the trachea. Preferably, the ventilation channel and the suction channel are oriented in the tube shaft such that the ventilation channel is on the anterior side and the suction channel is on the posterior side. Access to the esophagus is controlled through the suction channel, and access to the trachea is controlled through the ventilation channel.

One feature of the present invention is that the ventilation channel ends between the proximal and distal cuffs allowing the outside diameter of the tube shaft to be reduced at the distal cuff. This reduces the diameter of the non-tracheal ventilation tube that is inserted into the entrance of the esophagus of the patient which means less lifting of the larynx of the patient than would be required if the ventilation channel extended through the distal cuff which reduces the discomfort to the patient.

Another feature of the present invention is that the distal cuff can have an oval or elliptical shaped cross-section with the major axis extending laterally and the minor axis being in the anterior-posterior direction of the ventilation tube. The inflated elliptical-shaped distal cuff provides a gas and liquid tight seal at the entrance of the esophagus while avoiding unnecessary lifting of the larynx at the entrance to the esophagus. This more closely fits the anatomy of the patient which provides greater patient comfort and reduces recovery time.

Yet another feature of the present invention is that the suction channel has a generally circular or oval cross-section which has several advantages over a semi-circular or other cross-section having corners. The generally circular cross-section permits easy insertion and passage of a suction tube with a generally circular cross section of smaller outside diameter through the suction channel.

The generally circular cross-section also allows better utilization of the inside diameter of the tube shaft. By contouring the interior separating walls of the tube shaft closely to the inflation channel and the generally circular cross-section of the suction channel, the cross-section of the ventilation channel can be increased. This provides a greater space for exchange of respiratory gases, which is especially important for spontaneous breathing of the patient. This also allows the ventilation channel to extend over more than 180 degrees, half, of the perimeter of the tube shaft which allows respiratory apertures to be located along more than half of the circumference of the tube shaft reducing the chance of blockage of respiratory gases in the ventilation channel.

The generally circular cross-section of the suction channel also minimizes the transition necessary at the distal end of the tube shaft. When the suction channel extends beyond the end of the ventilation channel near the distal cuff, the outside diameter of the non-tracheal ventilation tube can be reduced to encompass the circular or oval cross-section of the suction channel at the distal end of the non-tracheal ventilation tube.

Another feature of the present invention is that some embodiments include a divider at the distal end of the ventilation channel that allows respiratory gases to enter and exit the ventilation channel. The use of the divider structure provides ventilation apertures on the top and sides of the ventilation channel as well as at the distal end which further reduces the chance of blocking respiratory gases in the ventilation channel.

These and other features of the present invention will become more apparent to those skilled in the art in connection with a review of the drawings and detailed description of the invention set forth below.

VI. BRIEF DESCRIPTION OF THE DRAWINGS

FIG. 2 is a top view of the non-tracheal ventilation tube;

FIG. 3 is a cross-section of the non-tracheal ventilation tube taken along the line III—III shown in FIG. 2;

FIG. 9 is a top view of another alternative embodiment of the non-tracheal ventilation tube;

FIG. 10 is a cross-section of the alternative embodiment of the non-tracheal ventilation tube shown in FIG. 9 taken along the line X—X shown in FIG. 9;

VII DETAILED DESCRIPTION

Figure 1:
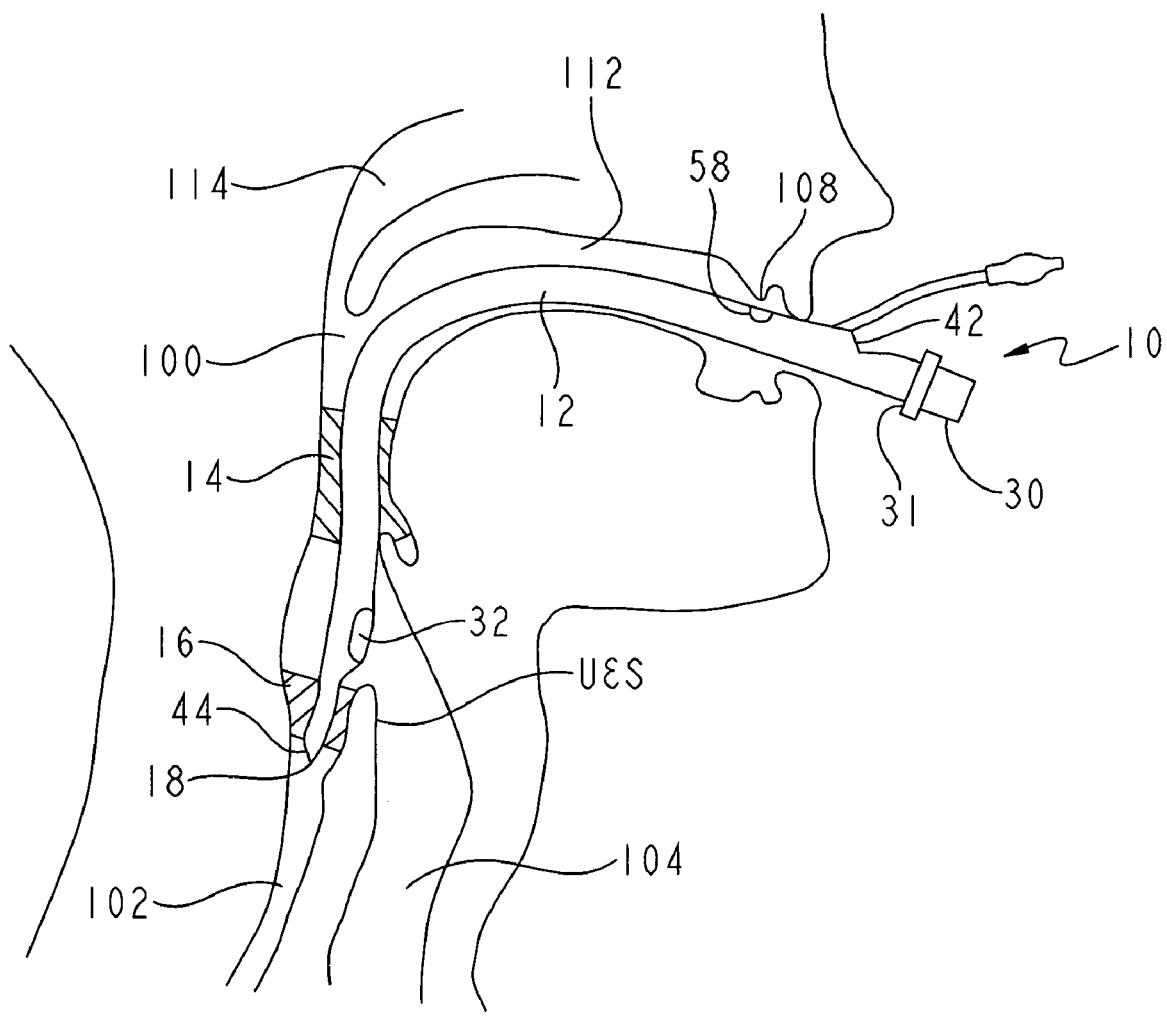
FIG. 1 is a schematic cut-through view of a non-tracheal ventilation tube introduced into the airway and esophagus of a patient.

FIG. 1 shows a non-tracheal ventilation tube 10 inserted into the airway 100 and extending into the esophagus 102 of a patient. The non-tracheal ventilation tube 10 comprises a multi-lumen tube shaft 12 having a distal end 18; and attached to the tube shaft 12 are an inflatable proximal cuff 14 and an inflatable distal cuff 16. The non-tracheal ventilation tube 10 preferably has an S-shaped longitudinal profile to help ensure that the distal end 18 of the non-tracheal ventilation tube 10 is introduced into the esophagus 102 and not into the trachea 104. The distal end 18 of the non-tracheal ventilation tube 10 is preferably made of a soft and flexible material for greater patient comfort. When properly introduced into the airway 100 of the patient, the inflated proximal cuff 14 blocks the trachea 104 from the nasopharynx 114 and the oropharynx 112, and the inflated distal cuff 16 blocks the trachea 104 from the esophagus 102.

Figure 4:
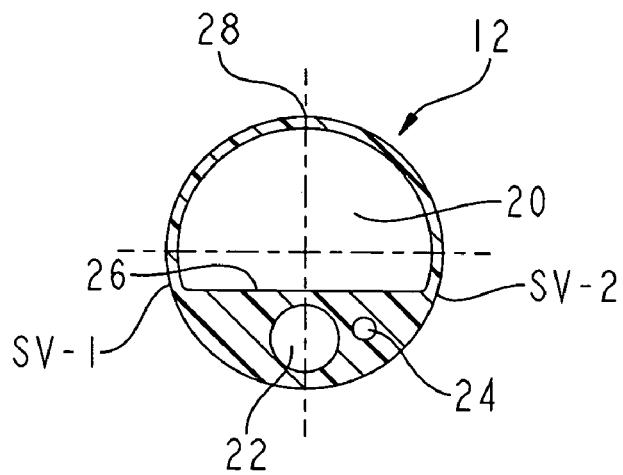
FIG. 4 is a cross-section of the non-tracheal ventilation tube taken along the line IV—IV shown in FIG. 2.

FIG. 2 shows a top-view of one embodiment of the non-tracheal ventilation tube 10, FIG. 3 shows a cross-section, side-view taken along the line III—III shown in FIG. 2, and FIG. 4 shows a cross-section of the multi-lumen tube shaft 12 taken along the line IV—IV shown in FIG. 2. The tube shaft 12, preferably made of a flexible elastic plastic, comprises a ventilation channel 20, a suction channel 22 and an inflation channel 24. Preferably, the ventilation channel 20 and the suction channel 22 are oriented in the tube shaft 12 such that the ventilation channel 20 is on the anterior side and the suction channel 22 is on the posterior side so that when the non-tracheal ventilation tube 10 is properly inserted in a patient's airway the ventilation channel 20 is on the tracheal side and the suction channel 22 is on the esophageal side of the patient's anatomy.

Additionally, the particular curve of the tube, along with the angle cut and position of the angle cut of the distal end 18 of the suction channel help to ensure that the tip 18 will enter the esophagus during a blind insertion. The flexibility of the tip 18 also aids in this process.

The interior walls of the shaft 12 prevent fluid communication between any of the three channels: the ventilation channel 20, the suction channel 22 or the inflation channel 24. Preferably, the tube shaft 12 has one insertion mark 58 (FIG. 1) or a plurality of insertion marks 58a, 58b, 58c (FIG. 2), forming a scale, to indicate when the non-tracheal ventilation tube 10 is inserted to the proper depth in a patient's airway.

The proximal cuff 14 and the distal cuff 16 are attached to the tube shaft 12 and are made from an elastic material, such as silicone or rubber, which expands and contracts as gases are added or removed through the inflation channel 24. The inflatable proximal and distal cuffs 14, 16 have a generally circular or oval shaped cross-section and can have a more specific anatomical shape to better conform to the surrounding anatomy of the patient. The cuffs 14, 16 are preferably high-volume, low-pressure cuffs that provide greater comfort for the patient. When the non-tracheal ventilation tube 10 is properly introduced into the airway 100 of the patient, the inflated proximal cuff 14 provides a gas and liquid tight seal on the proximal side of the entrance to the trachea 104, and the inflated distal cuff 16 provides a gas and liquid tight seal at the entrance of the esophagus 102 on the distal side of the entrance to the trachea 104. The proximal and distal cuffs 14, 16, when inflated, also provide stabilization of the non-tracheal ventilation tube 10 in the airway 100 of the patient.

Preferably, the ventilation channel 20, suction channel 22 and inflation channel 24 are formed simultaneously through co-extrusion. Alternately, the channels 20, 22, 24 can be formed as separate tubes that are later bonded together.

In the preferred embodiment, the distal cuff 16 has a generally oval or elliptical shaped cross-section with the major axis extending laterally and the minor axis being in the anterior-posterior direction of the ventilation tube 12. The inflated elliptical-shaped distal cuff 16 provides a gas and liquid tight seal at the entrance of the esophagus 102 while avoiding unnecessary lifting of the larynx at the entrance to the esophagus 102. This more closely fits the anatomy of the patient and provides greater patient comfort.

The proximal end of the inflation channel 24 is connected to an inflation tube 52 which is connected to an inflation valve 54. The inflation channel 24 has an inflation opening within the proximal cuff 14 and an inflation opening within the distal cuff 16. Thus, the two cuffs 14, 16 are interconnected by the inflation channel 24 which allows pressure compensation between the proximal cuff 14 and the distal cuff 16. The inflation valve 54 can be used for connecting conventional inflation/deflation devices and/or pressure measurement devices, such as a syringe or a cuff pressure gauge, to the inflation channel 24. Alternatively, the non-tracheal ventilation tube 10 could include two inflation channels with one going to the proximal cuff 14 and the other going to the distal cuff 16, allowing the two cuffs to be pressurized independently. In this case, each of the inflation channels would have separate inflation tubes connected to inflation valves.

Figure 4A:
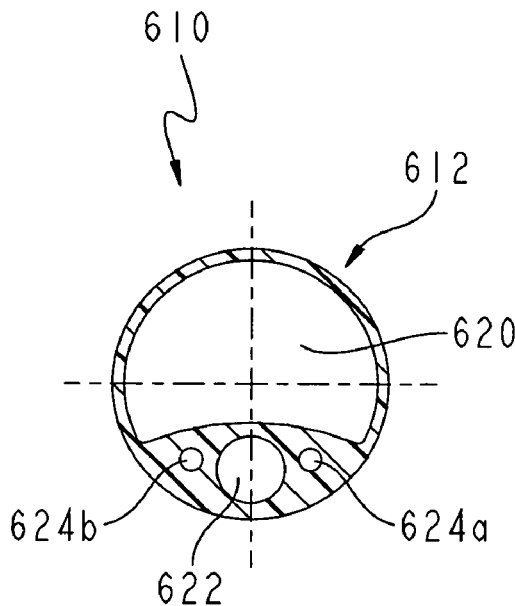
FIG. 4A is a cross-sectional view, similar to FIG. 4 of an alternative embodiment non-tracheal ventilation tube having a two inflation lines.

An example of such a two inflation channel containing alternate embodiment is shown in FIG. 4A. FIG. 4A shows a cross-section of a multi-lumen tube shaft 612 in a view that is generally similar in orientation to the view shown in FIG. 4. The tube shaft 612, is preferably made of a flexible elastic plastic, and includes a ventilation channel 620, a suction channel 622, a first inflation channel 624a and a second inflation channel 624b. The first inflation channel 624a controls the inflation and deflation of the proximal cuff (e.g. 14) and the second inflation channel 624b controls the inflation and deflation of the distal cuff (e.g. 16).

This individualized control is useful to the practitioner during the treatment of the patient in certain circumstances. For example, when a non-tracheal ventilation tube 610 that is already inserted in a patient, is being replaced with a tracheal tube, the proximal cuff (e.g. 14) can be deflated via the first inflation channel 624a, with the distal cuff remaining inflated. The practitioner can then slide the tracheal tube (not shown) along side the non-tracheal ventilation tube 610 to better insert the tracheal tube in the patient. As the distal cuff (e.g. 16) remains inflated due to the control exertable by second inflation channel 624b, the patient's esophagus will remain blocked during this process, thus reducing the likelihood of aspiration.

It has also been found that the use of the two inflation channels provides certain manufacturing advantages. It should further be noted that the ventilation channel of the alternate embodiment non-tracheal ventilation tube 610 shown in FIG. 4A has a crescent-like shape in cross section.

The ventilation channel 20 has a proximal end 31 and a distal end 33. A connector 30 is attached to the proximal end 31 of the ventilation channel 20 that can be used for connecting the ventilation channel 20 to conventional ventilation equipment. The distal end 33 of the ventilation channel 20 is located between the proximal cuff 14 and the distal cuff 16. The distal end of the ventilation channel 20 includes one or more primary ventilation apertures 32 which, when the non-tracheal ventilation tube 10 is properly inserted in the airway of a patient, face the trachea 104 of the patient. In the preferred embodiment, the non-tracheal ventilation tube 10 also includes one or more secondary ventilation apertures 38 located on the top or lateral sides of the ventilation channel 20. The ventilation apertures 32, 38 can have widely differing shapes, including circular, oval, slot shaped, tear-drop shaped and combinations of these shapes. Preferably, at least one of the ventilation apertures 32, 38 protrudes into the base of the proximal cuff 14 without interfering with the airtight nature of the proximal cuff 14, as shown in FIG. 2. The plurality of ventilation apertures 32, 38 helps prevent the epiglottis of the patient or other structures from causing significant blockage of the ventilation channel 20 that would compromise the patient's respiration through the ventilation channel 20.

A plug 34 having a ramped surface 36 is inserted in the distal end 33 of the ventilation channel 20 to cause substances passing through the ventilation channel 20 to exit through the ventilation apertures 32, 38. The ramped surface 36 of the plug 34 helps to direct the ends of catheters, fiberoptic scopes or other devices, when passed through the ventilation channel 20, to pass through one of the primary ventilation openings 32 and towards the entrance to the trachea 104. Thus, when the non-tracheal ventilation tube 10 is properly introduced into a patient, the connector 30 can be connected to a respiratory device that sends respiratory gases through the connector 30 into the proximal end 31 of the ventilation channel 20 towards the distal end 33 and to pass through the ventilation apertures 32, 38 into the trachea 104. Additionally, when tube 10 is properly inserted, catheters or other medical devices can be inserted through the connector 30 into the proximal end 31 of the ventilation channel 20 towards the distal end 33 to be deflected by the ramped surface 36 of the plug 34 to pass through one of the primary ventilation apertures 32 into the trachea 104.

The suction channel 22 extends from a proximal suction opening 42 located on the proximal side of the proximal cuff 14 to a distal suction opening 44 on the distal side of the distal cuff 16, near the distal end 18 of the non-tracheal ventilation tube 10. Preferably, the proximal suction opening 42 is a cut-away connection not requiring a separate connector for ease of manufacturing. Thus, when the non-tracheal ventilation tube 10 is properly introduced into a patient, the distal suction opening 44 is located in the entrance of the esophagus 102 so that the suction channel 22 provides an easily accessible passageway between the cut-away proximal suction opening 42, in or near the mouth of the patient, to the distal suction opening 44, at the entrance to the esophagus 102, permitting removal of secretions or foreign bodies from the esophagus 102 or stomach of the patient.

As seen in FIGS. 1–3, the distal end 33 of the ventilation channel 20 and of the plug 34 do not extend through the distal cuff 16. Rather, the distal end 33 of the ventilation channel 20 and plug 34 terminate proximally of the distal cuff 16. Only the suction channel 22 extends through the distal cuff 16 to the distal end 18 of the non-tracheal ventilation tube 10. Thus, the outside diameter of the tube shaft 12 extending through the distal cuff 16 and which is introduced into the opening of the esophagus 102 of the patient can be reduced to the outside diameter of the suction channel 22, giving this portion of the tube shaft 12 a reduced diameter, relative to the diameter of the tube shaft proximal thereof. This reduction in the diameter of the non-tracheal ventilation tube 10 that is inserted into the entrance of the esophagus 102 requires less lift of the larynx of the patient than would be required if the ventilation channel 20 extended through the distal cuff 16 which reduces the discomfort to the patient.

The suction channel 22 is preferably sized and shaped with a generally circular or oval cross-section. This permits easy insertion and passage of a suction tube with a generally circular cross section through the suction channel 22, allows better utilization of the inside diameter of the tube shaft 12, and minimizes the transition necessary from the proximal portion of the tube shaft 12, with both the ventilation channel 20 and the suction channel 22, to the distal portion of the tube shaft 12, with only the suction channel 22.

The suction channel 22 is generally used for passing a suction tube through the proximal opening 42 at or near the mouth of the patient through to the distal opening 44 in the esophagus 102. Suction tubes used for this application generally have a circular cross-section with standard adult sizes being 14, 16 and 18 French. Having a suction channel 22 with a generally circular cross-section, and a larger inside diameter than the outside diameter of the suction tube, permits easy passage of a suction tube through the suction channel 22 and into the esophagus 102. The generally circular cross-section of the suction tube 22 minimizes corners or smaller diameter sections that could potentially block or bind the suction tube as it is passed through the suction channel.

Having a suction channel 22 with a generally circular cross-section also allows better utilization of the inside diameter of the tube shaft 12, by maximizing the area that can be used for the ventilation channel 20 to provide respiratory gases to the patient. The inside diameter of the tube shaft 12 is separated into three lumens, with the largest lumens being used for the ventilation channel 20 and the suction channel 22. The size of the tube shaft 12 and the internal lumens are chosen based on the conflicting requirements that: (a) the tube shaft 12 be small enough to be inserted in the airway 100 and esophagus 102 of the patient with minimum damage or discomfort versus (b) the internal cross-section of the ventilation channel 20 be large enough to enable sufficient respiration by the patient, and (c) the internal cross-section of the suction channel 22 be large enough to clear fluid or solid materials from the esophagus 102 or stomach of the patient. Since the suction channel 22 is generally used for passing a suction tube through the proximal opening 42 at or near the mouth of the patient through to the esophagus 102, the suction channel 22 need only be large enough to permit passage of the desired suction tube. Thus, the suction channel 22 can be made of sufficient diameter to permit passage of standard suction tubes, and the remaining inside diameter of the tube shaft 12 can be utilized to maximize the ventilation channel 20.

FIG. 4, a cross-section of the tube shaft 12, shows more than half of the inside diameter of the tube shaft 12 is used for the ventilation channel 20 while leaving room for the generally circular or oval cross-section of the suction channel 22 and the inflation channel 24.

Figure 5:
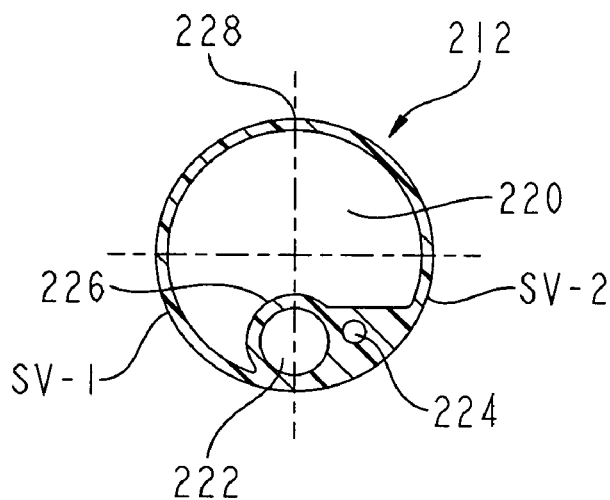
FIG. 5 is a cross-section of an alternative embodiment of the non-tracheal ventilation tube taken along the line IV—IV shown in FIG. 2.

FIG. 5 is a cross-sectional view of an alternative multi-lumen tube shaft 212 taken along the line IV—IV shown in FIG. 2. Similar to the tube shaft 12 shown in FIG. 4, the tube shaft 212 comprises a ventilation channel 220, a suction channel 222, an inflation channel 224, and a separating wall 226. The separating wall 226 of the shaft 212 prevents fluid communication between any of the three channels: the ventilation channel 220, the suction channel 222 or the inflation channel 224. The separating wall 226 is contoured to the outside diameter of the suction channel 222. Thus, with the suction channels 22 and 222 having the same diameter, the contoured separating wall 226 enables the ventilation channel 220 shown in FIG. 5 to have an even larger cross-sectional area than the ventilation channel 20 shown in FIG. 4.

Using a configuration similar to that shown in FIG. 4, it has been found that with a multi-lumen tube shaft having an outside diameter of 48 French and a single inflation channel, the suction channel can be sized to accept an 18 French suction tube while still leaving the ventilation channel with a 10 millimeter inside diameter equivalent area.

The lumen configurations shown in the tubes 12 and 212 of FIGS. 4 and 5 also enable the option of having secondary ventilation apertures 38 over more than half the circumference of the tube shaft 12. Due to the anterior/posterior arrangement of the ventilation channel 20/suction channel 22 in the tube 12, the tube 12 has an anterior crest 28 in the ventilation channel 20. As shown by the dashed axes positioned at the center of the tube shaft 12 in FIG. 4, secondary ventilation apertures 38 can made in the tube shaft 12 that are more than ninety degrees to either side of the anterior crest 228. For example, secondary ventilation channels can be placed at positions shown by the ends of illustrative lines SV-1 and SV-2 in FIGS. 4 and 5. Similarly, the dashed axes positioned at the center of the tube shaft 212 in FIG. 5 which show an anterior crest 228, indicate that secondary respiratory apertures 38 can be more than ninety degrees to either side of the anterior crest 228 (such as at positions SV-1 and SV-2), especially on the side of the tube 212 without the inflation channel 224. Having secondary ventilation openings 38 over more than one hundred eighty degrees (half) of the circumference of the tube 12, 212 further reduces the chance that the epiglottis of the patient or other structures would cause significant blockage of respiratory gases that would compromise the patient's respiration through the ventilation channel 20.

The following discusses the tube cross-section shown in FIG. 4 but applies equally to the alternative tube cross-section shown in FIG. 5. Prior to insertion of the non-tracheal ventilation tube 10 into the airway of a patient, both the proximal cuff 14 and the distal cuff 16 are fully deflated using the inflation valve 54. The non-tracheal ventilation tube 10 is then inserted into the airway to the proper position, preferably using alignment of the insertion mark or marks 58A, 58B, 58C (FIG. 2) with the front teeth 108 or other structure. The distal end 33 of the ventilation channel 20 can also act as a tactile stop point to help indicate when the non-tracheal ventilation tube 10 is properly positioned in the patient's airway. Conventional inflation and pressure measurement devices are then connected to the inflation valve 54 to inflate the cuffs 14, 16 using the inflation channel 24 to the desired pressures.

When the non-tracheal ventilation tube 10 is properly positioned, the proximal cuff 14 blocks the oropharynx 112 and the nasopharynx 114 from the openings of the esophagus 102 and trachea 104, and the distal cuff 16 blocks the opening of the esophagus 104 so that access to the esophagus 102 is controlled through the suction channel 22, and access to the trachea 104 is controlled through the ventilation channel 20. Also, when the non-tracheal ventilation tube 10 is properly positioned, the ventilation channel 20 is preferably on the anterior side of the non-tracheal ventilation tube 10 facing the tracheal side of the patient's anatomy and the suction channel 22 is preferably on the posterior side of the non-tracheal ventilation tube 10 facing the esophageal side of the patient's anatomy.

Figure 6:
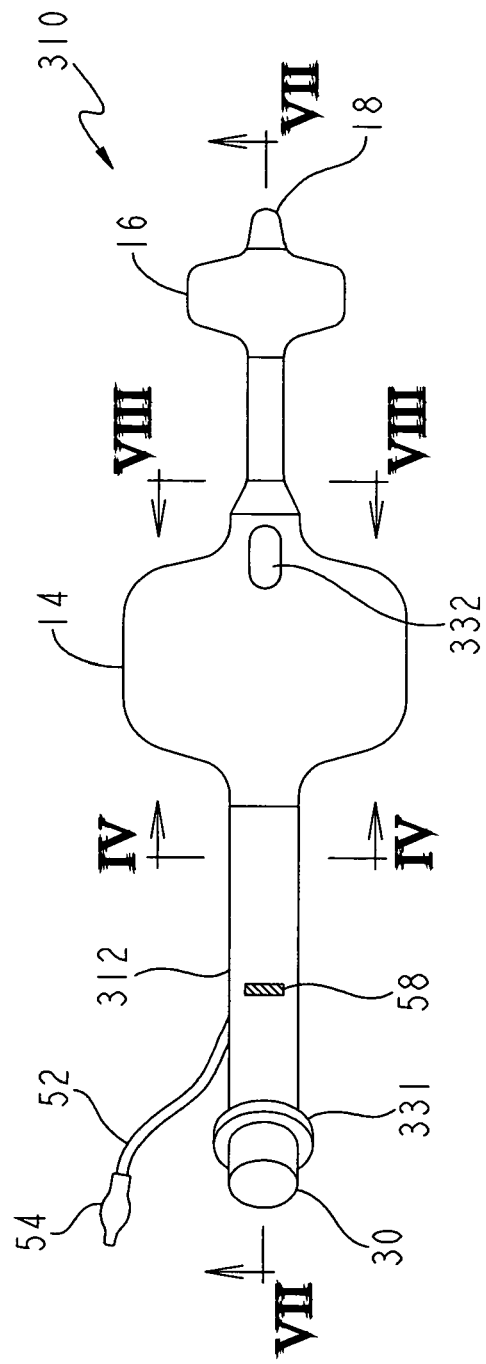
FIG. 6 is a top view of an alternative embodiment of the non-tracheal ventilation tube.
Figure 7:
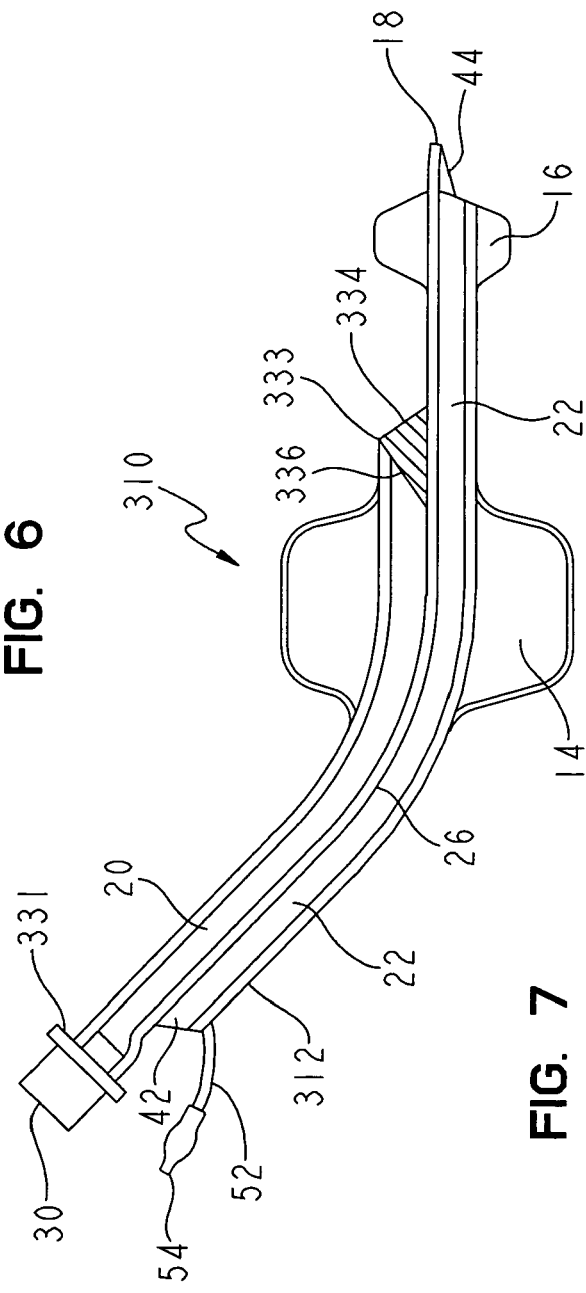
FIG. 7 is a cross-section of the alternative embodiment of the non-tracheal ventilation tube taken along the line VII—VII shown in FIG. 6.

FIG. 6 shows a top-view of a second embodiment of a non-tracheal ventilation tube 310, using the same element numbers for elements that are similarly constructed and utilized as explained for the first embodiment shown in FIG. 2. FIG. 7 shows a cross-section, side-view taken along the line VII—VII shown in FIG. 6. The cross-section of the multi-lumen tube shaft 312 could be as shown in either of FIG. 4 or 5 or another configuration comprising the ventilation channel 20, suction channel 22 and inflation channel 24, with the ventilation channel 20 and the suction channel 22 preferably oriented in an anterior-posterior relationship relative to each other. The interior walls of the shaft 312 prevent fluid communication between any of the three channels: the ventilation channel 20, the suction channel 22 or the inflation channel 24.

The ventilation channel 20 of the tube shaft 312 has a proximal end 331 and a distal end 333. The distal end 333 of the ventilation channel 20 is located adjacent to the distal end of the proximal cuff 14. A divider 334 having a ramped surface 336 is inserted in the distal end 333 of the ventilation channel 20. The distal end of the ventilation channel 20 includes a primary ventilation aperture 332 and can have one or more secondary ventilation apertures 338. The primary ventilation aperture 332, protrudes into the base of the proximal cuff 14 without interfering with the airtight nature of the proximal cuff 14. The primary ventilation aperture 332 is positioned at the anterior crest of the tube shaft 312 which, when the non-tracheal ventilation tube 310 is properly inserted in the airway of a patient, faces the opening of the trachea 104 of the patient. The distal end 333 of the ventilation channel 20 can act as a tactile stop point to help indicate when the non-tracheal ventilation tube 310 is properly positioned in the patient's airway.

Figure 8:
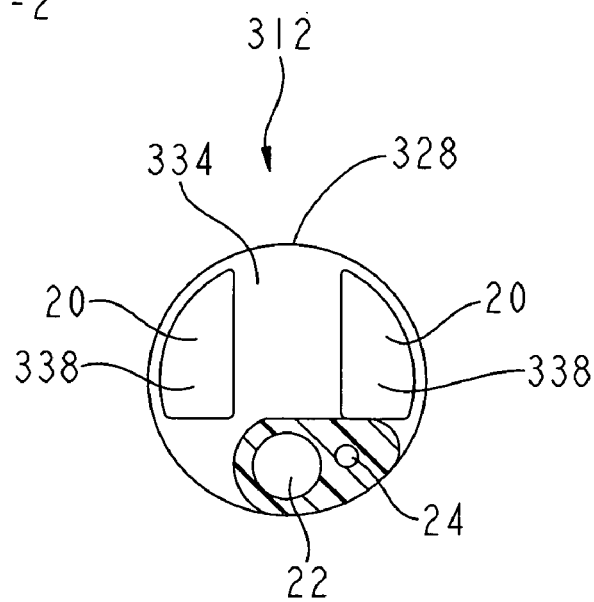
FIG. 8 is a cross-section of the non-tracheal ventilation tube taken along the line VIII—VIII shown in FIG. 6.

FIG. 8 shows a cross-section of the tube 312 taken along the line VIII—VIII of FIG. 6. As can be seen, the divider 334 does not completely block the distal end 333 of the ventilation channel 20. The ramped surface 336 on the proximal side of the divider 334 helps to direct the ends of catheters, fiberoptic scopes or other devices, when passed through the ventilation channel 20, to pass through the primary ventilation opening 332 and towards the entrance to the trachea 104. A through hole 338 on each side of the divider 334 allows respiratory gases to flow through the distal end 333 of the ventilation channel 20 and fluidly communicate with the trachea 104 of the patient. The divider 334 can also include interior openings as will be explained with reference to FIG. 13.

The ventilation channel 20 ends adjacent to the distal end of the proximal cuff 14, and only the suction channel 22 and the inflation channel 24 extend towards the distal cuff 16. Thus, as shown in FIG. 8, the outside perimeter of the tube shaft 312 extending towards the distal cuff 16 and which is introduced into the opening of the esophagus 102 of the patient is significantly reduced to the cross-hatched area 311 containing the suction channel 22 and the inflation channel 24. This reduction in the perimeter, and more precisely, this reduction in the A-P dimension of the non-tracheal ventilation tube 310 that is inserted into the entrance of the esophagus 102 requires less expansion of the entrance to the esophagus and less lift of the larynx of the patient than would be required if the ventilation channel 20 extended through the distal cuff 16. Using the distal cuff 16 with the preferred elliptical shape having the major lateral axis and the minor anterior-posterior axis, also aids in reducing the required expansion of the entrance to the esophagus and lift of the larynx which further reduces the discomfort to and recovery time of the patient.

FIG. 9 shows a top-view of a third embodiment of a non-tracheal ventilation tube 410, using the same element numbers for elements that are similarly constructed and utilized as explained for the earlier embodiments. FIG. 10 shows a cross-section, side-view taken along the line X—X shown in FIG. 9. The cross-section of the multi-lumen tube shaft 412 could be as shown in either of FIG. 4 or 5 or another configuration comprising the ventilation channel 20, suction channel 22 and inflation channel 24, with the ventilation channel 20 and the suction channel 22 preferably oriented in an anterior-posterior relationship relative to each other. The interior walls of the shaft 412 prevent fluid communication between any of the three channels: the ventilation channel 20, the suction channel 22 or the inflation channel 24.

The ventilation channel 20 of the tube shaft 412 has a proximal end 431 and a distal end 433. The distal end 433 of the ventilation channel 20 is located adjacent to the distal end of the proximal cuff 14. A divider 434 having a proximal ramped surface 436 and a distal extension 452 is coupled to the distal end 433 of the ventilation channel 20. The distal end of the ventilation channel 20 includes a primary ventilation aperture 432 and can have one or more secondary ventilation apertures 438. The primary ventilation aperture 432, can protrude into the base of the proximal cuff 14 but does not interfere with the airtight nature of the proximal cuff 14. The primary ventilation aperture 432 is positioned at the anterior crest of the tube shaft 412 so that, when the non-tracheal ventilation tube 410 is properly inserted in the airway of a patient, the primary ventilation aperture 432 faces the entrance to the trachea 104 of the patient.

Figure 11:
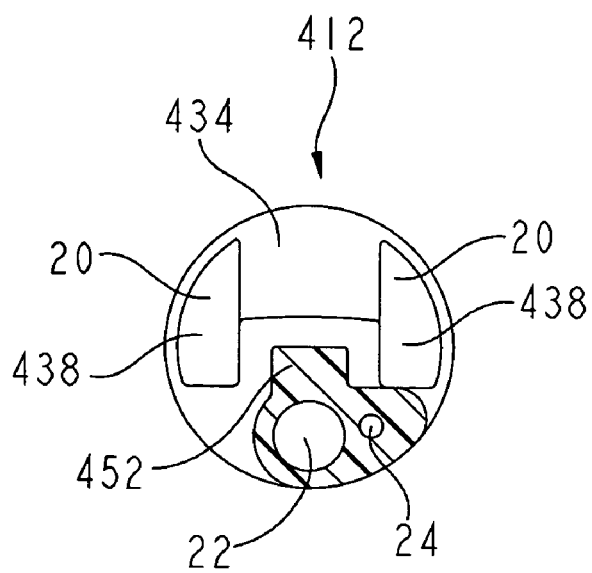
FIG. 11 is a cross-section of the non-tracheal ventilation tube taken along the line XI—XI shown in FIG. 9.

FIG. 11 shows a cross-section of the tube 412 taken along the line XI—XI of FIG. 9. As can be seen, the divider 434 does not completely block the distal end 433 of the ventilation channel 20. The ramped surface 436 on the proximal side of the divider 434 helps to direct the ends of catheters, fiberoptic scopes or other devices, when passed through the ventilation channel 20, to pass through the primary ventilation opening 432 and towards the entrance to the trachea 104. A pair of through holes 435, one on each side of the divider 434, allows respiratory gases to flow through the distal end of the ventilation channel 20 and fluidly communicate with the trachea 104 of the patient. The distal extension 452 extends distally from the divider 434 reducing in both height and width towards the distal cuff 16. When the non-tracheal ventilation tube 410 is ideally positioned in the airway of a patient, the distal end 433 of the ventilation channel 20 abuts the arytenoid cartilages and the extension 452 extends beyond the arytenoid cartilages of the patient. Thus, the distal end 433 of the ventilation channel 20 and divider 434 can act as a tactile stop point to help indicate when the non-tracheal ventilation tube 410 is properly positioned in the patient's airway.

Figure 13:
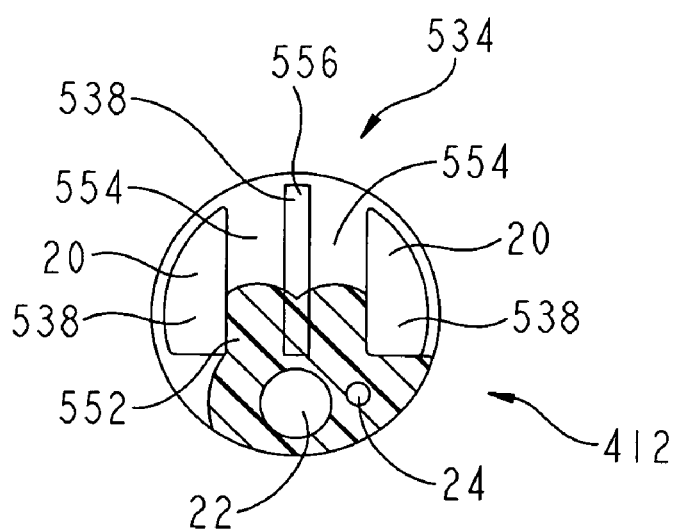
FIG. 13 is an alternate cross-section of the non-tracheal ventilation tube taken along the line XI—XI shown in FIG. 9.

FIG. 13 shows an alternative embodiment of a cross-section of the tube 412 taken along the line XI—XI of FIG. 9 with a grate divider 534. The grate divider 534 includes a proximal ramped shape surface (not shown) that is similar to the ramped shaped surface 436 of the divider 434. The grate divider 534 includes generally longitudinal members 554 and generally lateral members 556 which do not completely block the distal end 433 of the ventilation channel 20. The ramped surface (not shown) on the proximal side of the grate divider 534 helps to direct the ends of catheters, fiberoptic scopes or other devices, when passed through the ventilation channel 20, to pass through the primary ventilation opening 432 and towards the entrance to the trachea 104. The grate divider 534 provides a set of through holes 538 extending through the divider 534 between the generally longitudinal and lateral members 554, 556. The grate divider 534 can include vertical members, horizontal members, diagonal members, members at other varying angles, or combinations of these portions to define a mesh of through holes 538 at the distal end of the ventilation channel 20. The grate divider 534 can include a distal extension if desired.

Figure 12:
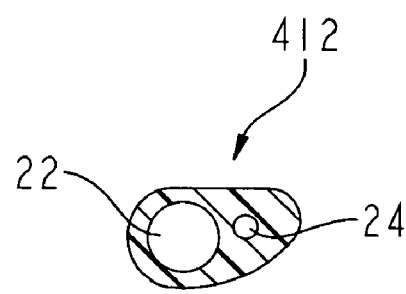
FIG. 12 is an alternative cross-section of the non-tracheal ventilation tube taken along the line XII—XII shown in FIG. 9.

FIG. 12 shows a cross-section of the tube 412 taken along the line XII—XII of FIG. 9. The ventilation channel 20 ends adjacent to the distal end of the proximal cuff 14, and only the suction channel 22 and the inflation channel 24 extend towards the distal cuff 16. Thus, as shown in FIG. 12, the outside perimeter of the tube shaft 412 extending towards the distal cuff 16 and which is introduced into the opening of the esophagus 102 of the patient is significantly reduced. This reduction in the perimeter (or more precisely, this reduction in the A-P dimension) of the non-tracheal ventilation tube 410 that is inserted into the entrance of the esophagus 102 requires less expansion of the opening of the esophagus and less lift of the larynx of the patient, and provides greater comfort and shorter recovery time for the patient than if the ventilation channel 20 extended through the distal cuff 16. Using the distal cuff 16 with the preferred elliptical shape having the major lateral axis and the minor anterior-posterior axis, also aids in reducing the required expansion of the entrance to the esophagus and lift of the larynx which further reduces the discomfort to and recovery time of the patient.

Figure 14:
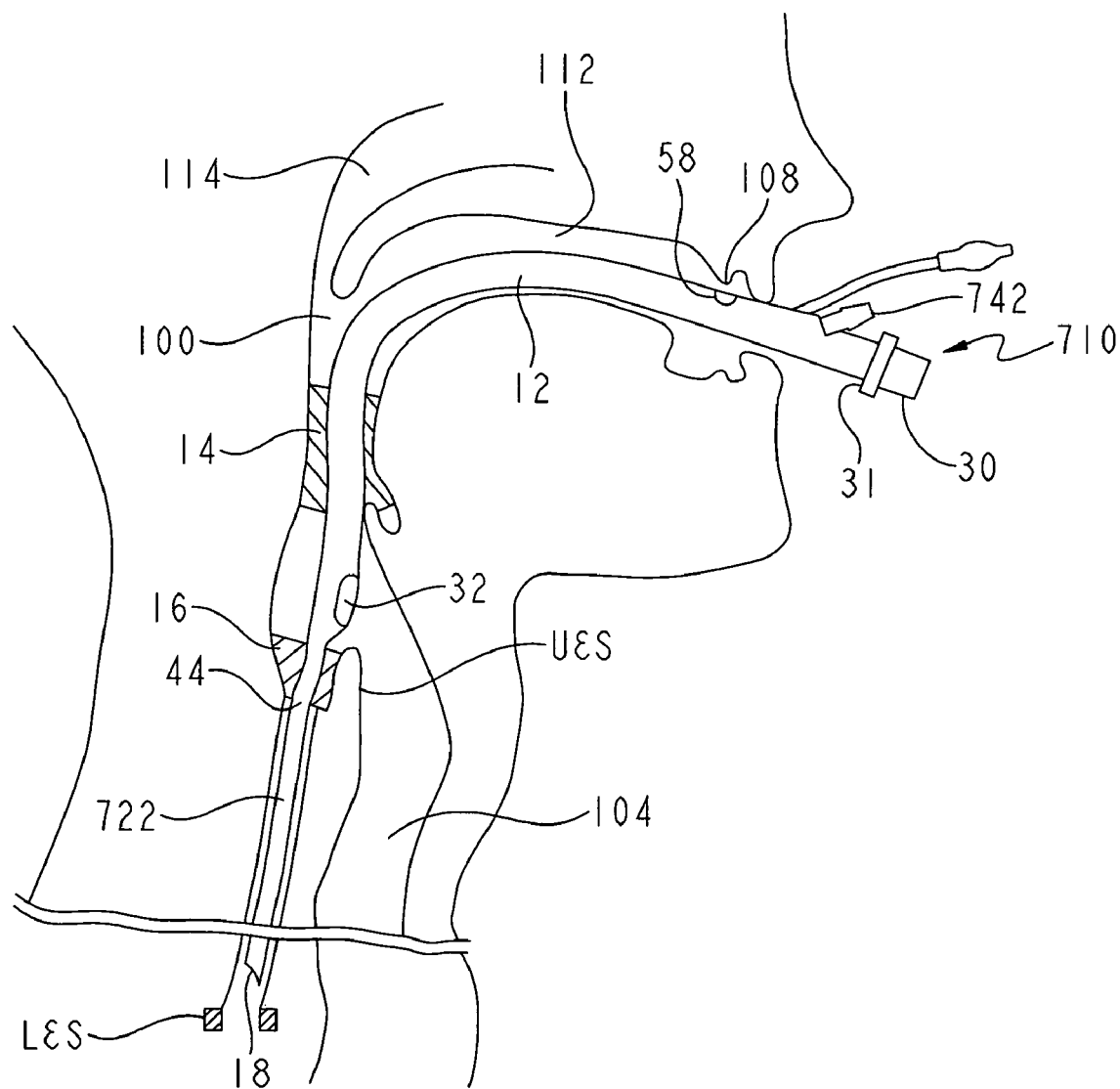
FIG. 14 is a schematic cut-through view of an alternate embodiment non-tracheal ventilation tube introduced into the airway and esophagus of a patient.

An alternate embodiment non-tracheal ventilation tube 710 is shown in FIG. 14. The non-tracheal ventilation tube 710 shown in FIG. 14 is generally similar to the non-tracheal ventilation tubes shown above in connection with FIGS. 1–13, with two important differences.

Comparing tube 710 of FIG. 14 to the tube 10 of FIG. 1, it will be noted that tube 710 includes a connector 742 that can be affixed at the proximal opening to the suction channel (e.g. 22 in FIG. 4, 222 in FIG. 5). This connector 742 permits a suction line to be directly affixed to the proximal end of the suction channel (e.g. 22), for better suctioning out debris, and other things from the gastrointestinal tract.

A second difference in tube 710 is the length of the suction channel 722. Turning now to FIG. 1, it will be noted that the distal end 18 of the suction channel 22 traverses the upper esophageal sphincter ("UES"), and extends about an inch or so into the opening of the esophagus. By contrast, the suction channel 722 of tube 710 extends substantially past the upper esophageal sphincter UES, perhaps by a distance of up to six inches or so. Although, in theory, the length of the suction channel 722 could be as long as desired, it is generally believed by the Applicants that the suction channel 722 should be of a length chosen so that the distal end 18 of the suction channel 722 does not traverse the lower esophageal sphincter muscle, LES.

One reason that one might wish to use such a extended suction tube is to create a suction tube having a greater diameter, to thereby provide a wider "space" through which fluids and other materials can pass.

One way that fluids and the like may be removed from the esophagus through the suction channel 722 is to insert a separate suction tube (not shown) into the suction channel 722, and then pass the suction tube out the end 18 of the suction channel 722 distally to a point wherein it can be in contact with the fluids that one seeks to remove. This tube within a tube arrangement, of course, limits the diameter of the inner suction tube. By using the suction channel 722 as the suction tube, there is no need to pass a separate suction tube (not shown) inside of the suction channel 722, thereby enabling the suction channel 722 to serve as a suction tube, and thereby giving the user the full diameter of the suction channel 722 to work with in suctioning out materials from the esophagus.

Figure 15:
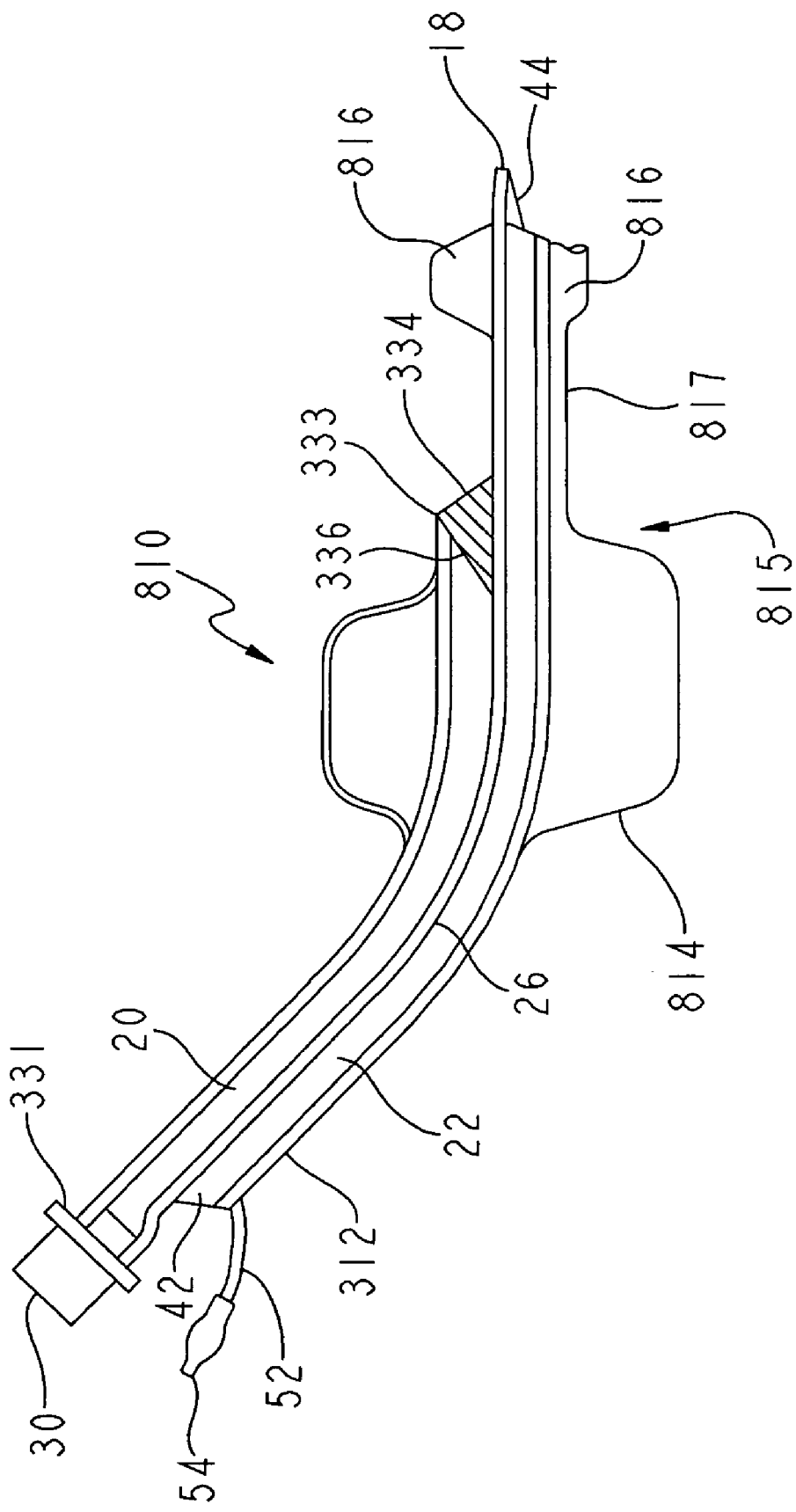
FIG. 15 is a cross section of another alternate embodiment of a non-tracheal ventilation tube showing a tube similar to the one shown in FIG. 7, with an alternate embodiment proximal and distal cuff.

FIG. 15 is a sectional view of an alternate embodiment tube 810 that is similar in most respects to tube 310 that is shown in FIG. 7. However, tube 810 includes a proximal cuff 814 and a distal cuff 816 that, while functionally separate, are unitarily formed. The proximal cuff 814 generally has a size and shape similar to proximal cuff 14; and distal cuff 16 generally has a size and shape similar to the distal cuff 16 shown in FIG. 7. However, the proximal 814 and distal 816 cuffs actually comprise proximal 814 and distal 816 cuff portions of a unitarily formed cuff 815.

A bridge portion 817 extends between proximal cuff 814 and distal cuff 816 to provide a channel through which air can travel to place the proximal cuff 814 and distal cuff 816 in fluid communication with each other. Even though the proximal cuff 814 and distal cuff 816 are formed as part of a unitary cuff 815, they still comprise a proximal cuff 814 and distal cuff 816 in the manner in which they function, insofar as the proximal cuff 814 is attached to the tube shaft and is connected to an inflation channel for inflation and deflation; and the distal cuff 816 is attached to the tube shaft on the distal side of the proximal cuff, and is connected to the inflation channel for inflation and deflation.

Having described the invention in detail, it will be appreciated that variations and modifications can exist within the scope and spirit of the invention as defined by the appended claims.

What is claimed is:

1. An non-tracheal ventilation tube comprising:
   a multi-lumen tube shaft having a proximal end and a distal end, said multi-lumen tube shaft being separated into a ventilation channel extending from a proximal ventilation opening to a distal ventilation opening, a suction channel extending from a proximal suction opening to a distal suction opening, and an inflation channel;
   a proximal cuff attached to said tube shaft and connected to said inflation channel for inflation and deflation;
   a distal cuff attached to said tube shaft on the distal side of said proximal cuff and connected to said inflation channel for inflation and deflation;
   said proximal suction opening and said proximal ventilation opening being located on the proximal side of said proximal cuff; said distal suction opening being located on the distal side of said distal cuff; said distal ventilation opening being located between said proximal cuff and said distal cuff; the outside diameter of said tube shaft decreasing between said proximal cuff and said distal cuff due to the ending of said ventilation channel.

2. The non-tracheal ventilation tube of claim 1 wherein said ventilation channel is located on the anterior side of said multi-lumen tube shaft and said suction channel is located on the posterior side of said multi-lumen tube shaft, whereby, when said non-tracheal ventilation tube is properly inserted in a patient, said ventilation channel faces the trachea of the patient and said suction channel is oriented to enter the esophagus of the patient.

3. The non-tracheal ventilation tube of claim 1 wherein the outside diameter of said tube shaft extending through said distal cuff is substantially equal to the outside diameter of said suction channel.

4. The non-tracheal ventilation tube of claim 1 wherein said distal cuff has a generally elliptical cross-section having a major axis extending laterally and a minor axis extending in an anterior-posterior direction.

5. The non-tracheal ventilation tube of claim 1 further comprising a plug inserted in the distal end of said ventilation channel, said plug having a proximal ramped surface inserted in said ventilation channel, said ramped surface directing substances coming from said proximal ventilation opening through said distal ventilation opening.

6. The non-tracheal ventilation tube of claim 1 further comprising:
   a divider having a proximal ramped surface inserted in the distal end of said ventilation channel, and
   a primary ventilation opening located near the distal end of said ventilation channel; said proximal ramped surface of said divider directing substances coming from said proximal ventilation opening through said primary ventilation opening, and said divider allowing the passage of ventilation gases through the distal end of said ventilation channel.

7. The non-tracheal ventilation tube of claim 6 wherein said divider comprises two or more members forming through holes between said members through which ventilation gases can pass.

8. The non-tracheal ventilation tube of claim 6 wherein said divider includes a distal extension extending along said multi-lumen tube shaft towards said distal cuff.

9. The non-tracheal ventilation tube of claim 1 wherein said distal ventilation opening comprises a primary ventilation opening and a plurality of secondary ventilation openings, said ventilation openings being located around more than 180 degrees of the circumference of said multi-lumen tube shaft.

10. The non-tracheal ventilation tube of claim 1 further comprising an interior separating wall separating said ventilation channel from said suction channel, said interior separating wall being contoured to maximize the cross-section of said ventilation channel.

11. The non-tracheal ventilation tube of claim 1 further comprising an interior separating wall separating said ventilation channel from said suction channel, said interior separating wall being contoured to maximize the cross-section of said ventilation channel.

12. The non-tracheal ventilation tube of claim 1 wherein the inflation channel comprises at least a first and a second inflation channel, wherein the first inflation channel is fluidly coupled to the proximal cuff for inflation and deflation of the proximal cuff, and the second inflation channel is fluidly coupled to the distal cuff for inflation and deflation of the distal cuff.

13. The non-tracheal ventilation tube of claim 1 wherein the ventilation channel is formed from a first tube, and the suction channel is formed from a second tube, the first and second tubes being bonded together to form the multi-lumen tube shaft.

14. The non-tracheal ventilation tube of claim 1, wherein the tube shaft includes a large diameter portion disposed proximally of the proximal cuff; a reduced diameter portion disposed distally of the distal cuff, the reduced diameter portion having an outer diameter less than an outer diameter of the large diameter portion; and a transition portion disposed between the proximal cuff and distal cuff.

15. The non-tracheal ventilation tube of claim 14 wherein the transition portion includes a relatively larger diameter portion disposed adjacent the proximal cuff and a relatively smaller diameter portion disposed adjacent to the distal cuff.

16. The non-tracheal ventilation tube of claim 14 wherein the distal cuff includes an inflatable portion for receiving gas from the inflation channel, the reduced diameter portion including a portion disposed distally of the inflatable portion of the distal cuff.

17. The non-tracheal ventilation tube of claim 1 further comprising a divider disposed at the distal end of the ventilation channel, the divider defining a pair of ventilation apertures disposed on the sides of the ventilation channel.

18. An non-tracheal ventilation tube comprising:
   a multi-lumen tube shaft having a proximal end and a distal end, a longitudinal extent extending in a direction between the proximal end and the distal end and a lateral extent extending in a direction generally perpendicular to the longitudinal extent, said multi-lumen tube shaft being separated into a ventilation channel, a suction channel having a generally circular cross-section, and an inflation channel, the multi-lumen tube shaft including an interior separating wall for separating said ventilation channel from said suction channel, said interior separating wall being contoured in a cross section taken along the lateral extent to maximize the lateral extent cross-sectional area of said ventilation channel;

a proximal cuff attached to said tube shaft and connected to said inflation channel for inflation and deflation;

a distal cuff attached to said tube shaft on the distal side of said proximal cuff and connected to said inflation channel for inflation and deflation;

wherein said ventilation channel has a proximal ventilation opening on the proximal side of said proximal cuff and a distal ventilation opening between said proximal cuff and said distal cuff; and said suction channel has a proximal suction opening on the proximal side of said proximal cuff and a distal suction opening on the distal side of said distal cuff.

19. The non-tracheal ventilation tube of claim 18 wherein the outside diameter of said tube shaft extending through said distal cuff is substantially equal to the outside diameter of said suction channel.

20. The non-tracheal ventilation tube of claim 18 wherein said distal cuff has at least one of a generally elliptical cross-section having a major axis and a minor axis, with the major axis extending laterally and the minor axis extending in an anterior-posterior direction and a generally circular cross section.

21. The non-tracheal ventilation tube of claim 18 further comprising a plug blocking the distal end of said ventilation channel, said plug having a proximal ramped surface inserted in said ventilation channel.

22. The non-tracheal ventilation tube of claim 18 further comprising a divider inserted at the distal end of said ventilation channel, said divider allowing the passage of ventilation gases through the distal end of said ventilation channel.

23. A non-tracheal ventilation tube comprising:
a multi-lumen tube shaft having a proximal end and a distal end, said multi-lumen tube shaft being separated into a ventilation channel, a suction channel having a generally circular cross-section, and an inflation channel, the multi-lumen tube shaft including an interior separating wall for separating said ventilation channel from said suction channel, said interior separating wall being contoured to maximize the cross-section of said ventilation channel;

a proximal cuff attached to said tube shaft and connected to said inflation channel for inflation and deflation;

a distal cuff attached to said tube shaft on the distal side of said proximal cuff and connected to said inflation channel for inflation and deflation;

wherein said ventilation channel has a proximal ventilation opening on the proximal side of said proximal cuff and a distal ventilation opening between said proximal cuff and said distal cuff; and said suction channel has a proximal suction opening on the proximal side of said proximal cuff and a distal suction opening on the distal side of said distal cuff and wherein the outside diameter of said tube shaft decreases between the distal side of said proximal cuff and the proximal side of said distal cuff.

24. A non-tracheal ventilation tube comprising:
a multi-lumen tube shaft having a proximal end and a distal end, said multi-lumen tube shaft being separated into a ventilation channel, a suction channel having a generally circular cross-section, and an inflation channel, the multi-lumen tube shaft including an interior separating wall for separating said ventilation channel from said suction channel, said interior separating wall being contoured to maximize the cross-section of said ventilation channel;

a proximal cuff attached to said tube shaft and connected to said inflation channel for inflation and deflation;

a distal cuff attached to said tube shaft on the distal side of said proximal cuff and connected to said inflation channel for inflation and deflation;

wherein said ventilation channel has a proximal ventilation opening on the proximal side of said proximal cuff and a distal ventilation opening between said proximal cuff and said distal cuff; and said suction channel has a proximal suction opening on the proximal side of said proximal cuff and a distal suction opening on the distal side of said distal cuff and further comprising a divider inserted at the distal end of said ventilation channel, said divider allowing the passage of ventilation gases through the distal end of said ventilation channel wherein said divider comprises two or more members defining through holes between said members through which ventilation gases can pass.

25. The non-tracheal ventilation tube of claim 24 wherein said divider includes a distal extension extending along said multi-lumen tube shaft towards said distal cuff.

26. A non-tracheal ventilation tube comprising:
a multi-lumen tube shaft having a proximal end and a distal end, said multi-lumen tube shaft being separated into a ventilation channel, a suction channel having a generally circular cross-section, and an inflation channel, the multi-lumen tube shaft including an interior separating wall for separating said ventilation channel from said suction channel, said interior separating wall being contoured to maximize the cross-section of said ventilation channel;

a proximal cuff attached to said tube shaft and connected to said inflation channel for inflation and deflation;

a distal cuff attached to said tube shaft on the distal side of said proximal cuff and connected to said inflation channel for inflation and deflation;

wherein said ventilation channel has a proximal ventilation opening on the proximal side of said proximal cuff and a distal ventilation opening between said proximal cuff and said distal cuff; and said suction channel has a proximal suction opening on the proximal side of said proximal cuff and a distal suction opening on the distal side of said distal cuff and wherein said distal ventilation opening comprises a primary ventilation opening and a plurality of secondary ventilation openings, said ventilation openings being located around more than 180 degrees of the circumference of said multi-lumen tube shaft.

27. An non-tracheal ventilation tube comprising:
a multi-lumen tube shaft having a proximal end and a distal end, said multi-lumen tube shaft being separated into a ventilation channel extending from a proximal ventilation opening to a distal ventilation opening, a suction channel extending from a proximal suction opening to a distal suction opening, and an inflation channel;

a proximal cuff attached to said tube shaft and connected to said inflation channel for inflation and deflation;

a distal cuff having a generally elliptical cross-section with the major axis extending laterally and the minor axis extending in the anterior-posterior direction, said distal cuff attached to said tube shaft on the distal side of said proximal cuff and connected to said inflation channel for inflation and deflation;

said proximal suction opening and said proximal ventilation opening being located on the proximal side of said proximal cuff; said distal suction opening being located on the distal side of said distal cuff; said distal ventilation opening being located between said proximal cuff and said distal cuff; the outside diameter of said tube shaft decreasing between said proximal cuff and said distal cuff due to the ending of said ventilation channel.

28. The non-tracheal ventilation tube of claim 27 wherein the outside diameter of said tube shaft decreases between the distal side of said proximal cuff and the proximal side of said distal cuff.

29. The non-tracheal ventilation tube of claim 28 wherein said suction channel has a generally circular cross-section.

30. A non-tracheal ventilation tube comprising:
a multi-lumen tube shaft having a proximal end and a distal end, said multi-lumen tube shaft being separated into a ventilation channel, a suction channel having a generally circular cross-section, and an inflation channel, the multi-lumen tube shaft including an interior separating wall for separating said ventilation channel from said suction channel, said interior separating wall being contoured to maximize the cross-section of said ventilation channel;
a proximal cuff attached to said tube shaft and connected to said inflation channel for inflation and deflation;
a distal cuff attached to said tube shaft on the distal side of said proximal cuff and connected to said inflation channel for inflation and deflation;
wherein said ventilation channel has a proximal ventilation opening on the proximal side of said proximal cuff and a distal ventilation opening between said proximal cuff and said distal cuff; and said suction channel has a proximal suction opening on the proximal side of said proximal cuff and a distal suction opening on the distal side of said distal cuff and
wherein the suction channel formed by the contoured interior separating wall has one of an elliptical and circular cross section.

* * * * *